US00PP16502P2

(12) United States Plant Patent
Olesen

(10) Patent No.: US PP16,502 P2
(45) Date of Patent: May 2, 2006

(54) CLIMBING ROSE PLANT NAMED 'POULCY012'

(50) Latin Name: ***Rosa* hybrid**
Varietal Denomination: Poulcy012

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 85 days.

(21) Appl. No.: 11/002,359

(22) Filed: Dec. 1, 2004

(51) Int. Cl.
*A01H 5/00* (2006.01)

(52) U.S. Cl. ..... Plt./115
(58) Field of Classification Search ..... Plt./115, Plt./114
See application file for complete search history.

*Primary Examiner*—Anne Marie Grunberg
*Assistant Examiner*—June Hwu

(57) ABSTRACT

A new garden rose plant of the climbing rose class which has abundant, red flowers and attractive, dark, glossy foliage. This new and distinct variety has shown to be uniform and stable in the resulting generations from asexual propagation.

1 Drawing Sheet

Botanical classification: *Rosa* hybrid.
Variety denomination: 'Poulcy012'.

SUMMARY OF THE INVENTION

The present invention constitutes a new and distinct variety of garden rose plant that originated from a controlled crossing between the female seed parent 'Kormixal', an unpatented variety, and the male pollen parent, an un-named seedling from the same inventors.

The two parents were crossed during the summer of 1994 and the resulting seeds were planted in a controlled environment in Fredensborg, Denmark. The new variety is named 'Poulcy012'.

The new variety may be distinguished from its female seed parent, 'Kormixal' by the following combination of characteristics:

1. 'Poulcy012' is taller than the seed parent.
2. 'Kormixal' has fewer flower petals than 'Poulcy012'.
3. 'Kormixal' has smaller flowers than 'Poulcy012'.

The new variety may be distinguished from the male pollen parent by the following combination of characteristics:

1. The pollen parent has light pink flowers while 'Poulcy012' has medium red flowers.
2. 'Poulcy012' produces a greater quantity of flowers than the pollen parent.

The objective of the hybridization of this rose variety was to create a new and distinct variety for garden use with unique qualities, such as:

1. Uniform and abundant medium red flowers;
2. Vigorous, but compact growth when propagated both as a budded rose and on its own roots;
3. Disease resistance.
4. Reduced apical dominance in flowering habit. The new variety consistently produces flowers evenly from the lower branches to the top of the plant.

This combination of qualities is not present in previously available commercial cultivars of this type, known to the inventors, and distinguish 'Poulcy012' from all other varieties of which we are aware.

As part of the rose development program, Mogens N. Olesen germinated the seeds from the aforementioned hybridization during winter of 1996 and conducted evaluations on the resulting seedlings in a controlled environment in Fredensborg, Denmark.

'Poulcy012' was selected in the spring of 1997 by the inventor as a single plant from the progeny of the aforementioned hybridization.

Asexual reproduction of 'Poulcy012' by traditional budding and rooted cuttings was first done by Mogens N. Olesen in the nursery in Fredensborg, Denmark in July 1997. This initial and other subsequent asexual propagations conducted in controlled environments have demonstrated that the characteristics of 'Poulcy012' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcy012'. Specifically illustrated in the drawing:

FIG. 1.1; Open flowers;

FIG. 1.2; Sepals, receptacle, and pedicel;

FIG. 1.3; Stem showing branching, and the attachment of leaves, buds, and peduncles;

FIG. 1.4; Petals detached;

FIG. 1.5; Juvenile and mature bare stems exhibiting thorns;

FIG. 1.6; Juvenile foliage;

FIG. 1.7; Mature foliage.

DETAILED DESCRIPTION OF THE VARIETY

The following is a description of 'Poulcy012', as observed in its growth in in a field nursery in Jackson County, Oreg. Observed plants are 2 years of age, and were grown on *Rosa multiflora* understock. Color references are made using The Royal Horticultural Society (London, England) Colour Chart, 1995, except where common terms of color are used.

For a comparison, several physical characteristics of the rose variety 'Poulyc009', a rose variety from the same inventors described and illustrated in U.S. Plant Pat. No. 15,411 issued on 7 Dec. 2004, are compared to 'Poulcy012' in Chart 1.

CHART 1

| | 'Poulcy012' | 'Poulyc009' |
|---|---|---|
| General tonality. | Red-Purple Group 58B to Red-Purple Group 57A. | Red-Purple Group 58B to 58C. |
| Flower diameter | 40 to 45 mm | 70 mm |
| Petal count | 40 | 25 |

FLOWER AND FLOWER BUD

Blooming habit: Recurrent.

Flower bud:

*Normal Size.*—Upon opening, 13 mm in length from base of receptacle to end of bud. Bud diameter is 9 mm.

*Bud form.*—Pointed ovoid with a broad base.

*Bud color.*—As sepals unfold, petals are Red Group 53C to Red-Purple Group 57A.

*Sepal inner surface.*—Color: Yellow-Green Group 147C. Surface: Somewhat pubescent.

*Sepal outer surface.*—Color: Yellow-Green Group 146A. Anthocyanic pigments Greyed-Purple Group 183A. Texture: Rough with many stipitate glands.

*Sepal shape.*—Apex: Cirrhose. Base: Flat at union with receptacle.

*Sepal margin.*—Many stipitate glands along margins. Margins have rough foliaceous appendages on three of the five sepals.

*Sepal size.*—15 mm (l) by 5 mm (w).

*Receptacle.*—Texture: Smooth. Shape: Funnel shaped. Size: 4 mm (l)×5 mm (w). Color: Yellow-Green Group 146B. Anthocyanic pigments the color of Greyed-Purple Group 183A observed.

*Pedicel.*—Surface: Rough with numerous stipitate glands. Stipitate glands produce strong fragrance when touched. Length: 18 to 25 mm. Diameter: 2 to 2.5 mm. Color: Yellow-Green Group 146B. Anthocyanic pigments Greyed-Purple 183A. Strength: Strong and erect.

Flower bud development: Flower buds are borne in clusters of 13 flower buds per stem. Inflorescence type is raceme. Reduced apical dominance in flower habit causes flower buds develop evenly from the base of the plant to the upper branches.

Flower bloom:

*Fragrance.*—Light floral scent.

*Duration.*—The blooms have a duration on the plant of approximately 10 days. Petals fall cleanly away from plant after flowers have fully matured.

*Size.*—Flower diameter is 40 to 45 mm when open. Flower depth is 15 mm on average.

*Flower shape.*—General shape is rosette with many overlapping petals.

*Shape of flower, side view.*—Upon opening, Upper portion: Flat. Lower portion: Concave. After opening, Upper portion: Flattened convex. Lower portion: Concave.

Petalage: Under normal conditions, flowers have 40 petals total, 15 of which are petaloids.

Petal color:

*Upon opening, outer petals.*—Upper surface: Red Group 52A. Occasional streaks of Red-Purple Group 58D to Red Group 52D and Yellow Group 4D observed. Lower surface: Red-Purple Group 58B to Red-Purple Group 57A. Occasional streaks of Red-Purple Group 58D to Red Group 52D observed.

*Upon opening, inner petals.*—Upper surface: Red Group 52A. Occasional streaks of Red-Purple Group 58D to Red Group 52D and Yellow Group 4D observed. Lower surface: Red-Purple Group 58B to Red-Purple Group 57A. Occasional streaks of Red-Purple Group 58D to Red Group 52D observed.

*Basal petal spots, upon opening.*—Upper surface: Yellow Group 6B. Lower surface: Yellow Group 4A.

*After opening, outer petals.*—Upper surface: Red Group 52A with intonations of Red Group 53B. Occasional streaks of Red Group 52D and Yellow Group 4D. Lower surface: Red-Purple Group 58B to Red-Purple Group 57A. Occasional streaks of Red-Purple Group 58D to Red Group 52D.

*After opening, inner petals.*—Upper surface: Red Group 52A with intonations of Red Group 53B. Occasional streaks of Red Group 52D and Yellow Group 4D. Lower surface: Red-Purple Group 58B to Red-Purple Group 57A. Occasional streaks of Red-Purple Group 58D to Red Group 52D.

*Basal petal spots, after opening.*—Upper surface: Yellow Group 6B. Lower surface: Yellow Group 4A.

General tonality: On open flower Red-Purple Group 58B to 57A. No change in tonality at the end of the $10^{th}$ day. Afterwards, general tonality becomes Red-Purple Group 66A.

Petals:

*Petal reflex.*—Slightly at flowers mature.

*Margin.*—Medium undulations of margin observed.

*Shape.*—Broad elliptical with occasional cleft at center of the margin. Apex: Rounded to emarginate. Base: Obtuse to acute.

*Size.*—Normally 15 mm (l)×16 mm (w).

*Texture.*—Smooth.

*Thickness.*—Average.

*Arrangement.*—Not Formal.

Petaloids:

*Quantity.*—15.

*Shape.*—Asymmetric. Apex: Acute. Base: Rounded.

*Color.*—Upper surface: Red Group 52A. Occasional streaks of Red-Purple Group 58D to Red Group 52D and Yellow Group 4D. Lower surface: Red-Purple Group 58B to Red-Purple Group 57A. Occasional streaks of Red-Purple Group 58D to Red Group 52D observed.

Size.—13 mm (l)×5 mm (w).

Reproductive organs:

*Pollen.*—None observed.

*Anthers.*—Size: 1 mm in length. Color: Yellow-Orange Group 17A. Quantity: 50 to 55 on average.

*Filaments.*—Color: Yellow Group 5A. Length: 5 mm.

*Pistils.*—Length: 4 to 5 mm. Quantity: 45 to 50 on average.

*Stigmas.*—Superior in location relative to the length of the filaments and the height of the anthers. Color: Yellow-Green Group 145B.

*Styles.*—Color: Yellow-Green Group 145B.

*Hips.*—None Observed in the field nursery in Jackson County Oreg.

PLANT

Plant growth: Climbing. When grown as a budded field grown plant on *Rosa multiflora* understock, the average height of the plant is 150 to 200 cm. Average spread is 100 cm.

Stems:

*Color.*— Juvenile growth: Yellow-Green Group 146B with anthocyanic intonations of Greyed-Orange 176B. Mature growth: Yellow-Green Group 146B.

*Length.*—On average, canes are 150 cm from the base of the plant to the flowering portion.

*Diameter.*—7 mm.

*Internodes.*—On mature canes, there is an average distance of 45 mm between nodes.

*Surface texture.*—Young wood: Rough. Older wood: Rough.

Thorns:

*Incidence.*—15 thorns per 10 cm of stem. Numerous smaller thorns or prickles are 2 to 3 mm in length.

*Length.*—10 mm.

*Shape.*—Upper side: Concave. Lower side: Deeply concave.

*Juvenile thorns.*—Color: Greyed-Purple Group 183A.

*Mature thorns.*—Color: Greyed-Orange Group 165C with intonations of Greyed-Orange Group 166B.

Plant foliage: Normal number of leaflets in middle of the stem: 7.

*Compound leaf.*—90 mm (l)×60 mm (w).

*Quantity.*—2 leaves per 10 cm of stem on average.

*Color of mature foliage.*—Upper side: Yellow-Green Group 147A. Lower side: Yellow-Green Group 147B.

*Color of juvenile foliage.*—Upper side: Yellow-Green Group 144A with marginal anthocyanic intonations of Greyed-Orange Group 175A. Lower side: Yellow-Green Group 146C with generalized anthocyanic intonations of Greyed-Orange Group 176B.

Plant leaves and leaflets:

*Stipules.*—Size: 13 mm in length. Shape: Linear, slightly broad based with outward extending apecies. Margins: Finely serrated with few stipitate glands. Color: Yellow-Green Group 146B.

*Petiole.*—Length: 18 mm. Diameter: 2 mm.

*Upper surface.*—Color: Greyed-Yellow Group 160D with pale intonation of Greyed-Red Group 180B.

*Lower surface.*—Color: Yellow-Green Group 146C. Observations: Few stipitate glands and few small prickles observed.

*Rachis.*—Length: 42 mm. Upper surface: Color: Yellow-Green Group 146A. Lower surface: Color: Yellow-Green Group 146C. Observations: Few stipitate glands and few small prickles observed.

*Leaflet.*—Edge: Serrated. Size: Average size of the terminal leaflet on normal leaves is 25 mm (l)×22 mm (w). Shape: Generally elliptical to rounded. Base: Obtuse. Apex: Cuspidate. Texture: Smooth. Thickness: Average. Arrangement: Odd pinnate. Venation: Reticulate. Glossiness: Very glossy.

Disease resistance: Above average resistance to powdery and downy mildews, rust, black spot, and *Botrytis* under normal growing conditions in Jackson County, Oreg.

Cold hardiness: The variety 'Poulcy012' has been found to be cold tolerant to USDA Cold Hardiness Zone 6.

It is claimed:

1. A new and distinct variety of rose plant of the climbing rose class named 'Poulcy012', substantially as illustrated and described herein as a distinct and novel rose variety due to its abundant red flowers, dark, glossy, attractive foliage, disease resistance, and extended period of bloom.

* * * * *

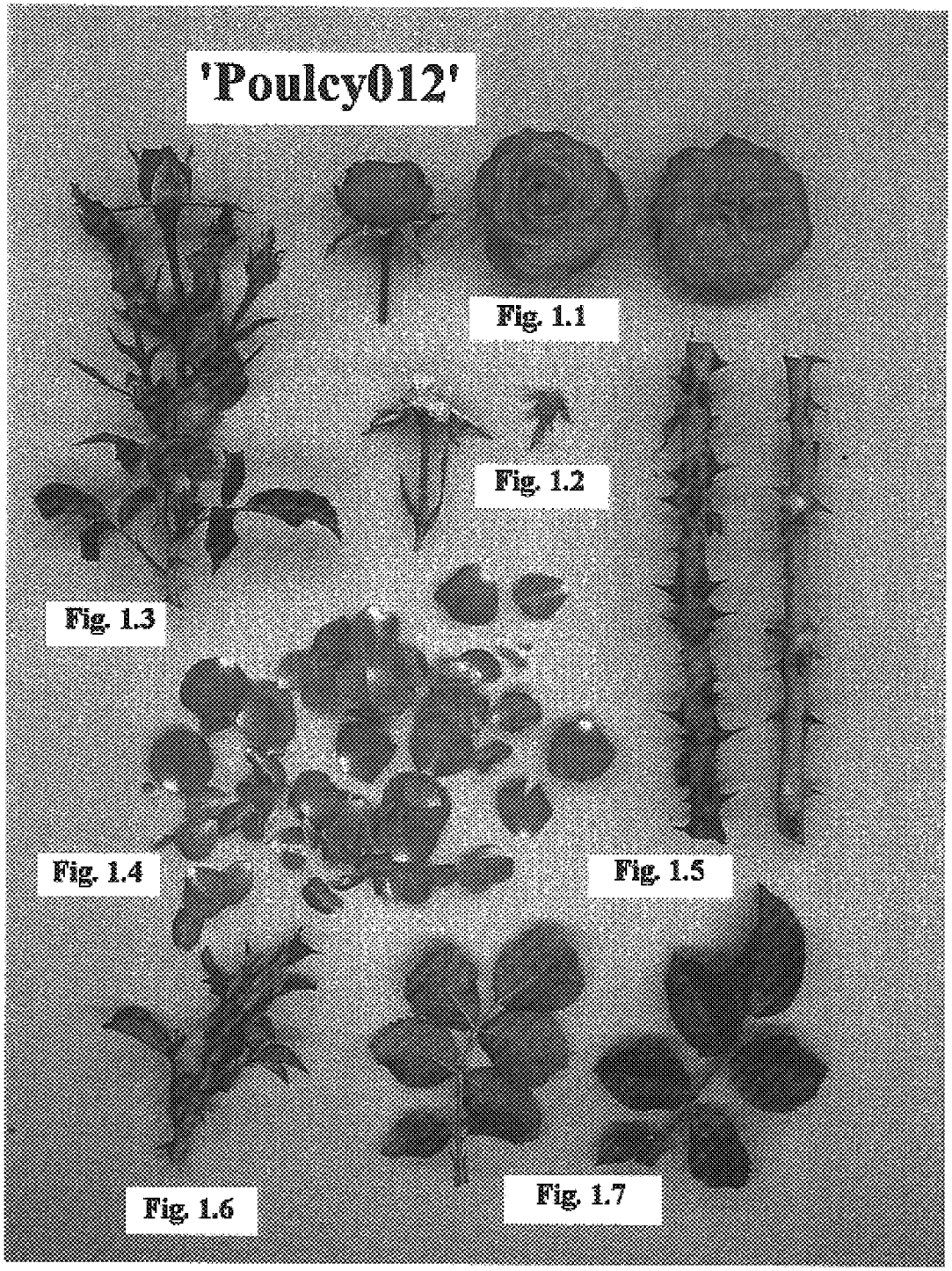
'Poulcy012'
Fig. 1.1
Fig. 1.2
Fig. 1.3
Fig. 1.4
Fig. 1.5
Fig. 1.6
Fig. 1.7